United States Patent

Greindl et al.

[11] Patent Number: 5,849,950
[45] Date of Patent: Dec. 15, 1998

[54] PREPARATION OF GLYCINE-N,N-DIACETIC ACID DERIVATIVES

[75] Inventors: Thomas Greindl, Neuburg; Alfred Oftring, Bad Dürkheim; Gerold Braun, Ludwigshafen; Jochen Wild, Ruppertsberg; Birgit Potthoff-Karl; Georg Schuh, both of Ludwigshafen, all of Germany

[73] Assignee: BASF Aktiengesellschaft, Ludwigshafen, Germany

[21] Appl. No.: 653,024

[22] Filed: May 24, 1996

[30] Foreign Application Priority Data

May 29, 1995 [DE] Germany .................. 195 18 986.8

[51] Int. Cl.$^6$ .................................... C07C 229/00
[52] U.S. Cl. .................. 562/571; 562/565; 562/572
[58] Field of Search .................. 562/565, 571, 562/512

[56] References Cited

U.S. PATENT DOCUMENTS

| | | |
|---|---|---|
| 2,500,019 | 3/1950 | Bersworth . |
| 3,668,246 | 6/1972 | Berding .................. 562/572 |
| 3,689,543 | 9/1972 | Berding .................. 562/572 |
| 3,733,355 | 5/1973 | Harris et al. . |
| 5,019,296 | 5/1991 | Baur .................. 252/546 |
| 5,177,243 | 1/1993 | Parker .................. 558/442 |
| 5,481,018 | 1/1996 | Athey .................. 558/442 |
| 5,543,566 | 8/1996 | Takahashi .................. 562/571 |

FOREIGN PATENT DOCUMENTS

| | | |
|---|---|---|
| 1284635 | 8/1972 | United Kingdom . |
| WO 94/29421 | 12/1994 | WIPO . |

*Primary Examiner*—Michael L. Shippen
*Attorney, Agent, or Firm*—Oblon, Spivak, McClelland, Maier & Neustadt, P.C.

[57] ABSTRACT

Glycine-N,N-diacetic acid derivatives I

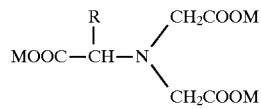 (I)

where

R is unsubstituted or substituted alkyl, alkenyl, alkoxylate groups, phenylalkyl, phenyl, a heterocyclic ring or a radical of the formula

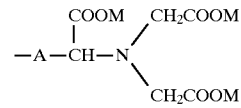

where A is an alkylene bridge or a chemical bond, and M is hydrogen, alkali metal, alkaline earth metal, ammonium or substituted ammonium in the appropriate stoichiometric amounts, are prepared by reacting A) corresponding 2-substituted glycines or 2-substituted glycinonitriles or doubled glycines of the formula

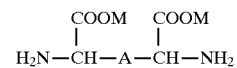

or doubled glycinonitriles of the formula

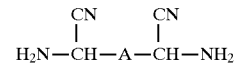

or precursors of the glycine derivatives named as starting material with formaldehyde and hydrogen cyanide in aqueous medium at a pH of from 0 to 11 or B) iminodiacetonitrile or iminodiacetic acid with appropriate monoaldehydes of the formula R—CHO or dialdehydes of the formula OHC—A—CHO and hydrogen cyanide in aqueous medium at a pH of from 0 to 11 and, where appropriate, subsequent hydrolysis of nitrile functionalities which are present, where the starting material used comprises unpurified raw material derived from the industrial synthesis of glycine derivatives or their precursors or of iminodiacetonitrile or iminodiacetic acid, or mother liquors produced in such syntheses.

5 Claims, No Drawings

PREPARATION OF GLYCINE-N,N-DIACETIC ACID DERIVATIVES

The present invention relates to an improved process for preparing glycine-N,N-diacetic acid derivatives by reacting glycine derivatives or their precursors with formaldehyde and hydrogen cyanide, or iminodiacetonitrile or iminodiacetic acid with appropriate aldehydes and hydrogen cyanide in aqueous acidic medium.

The standard products currently used in the typical applications of complexing agents and builders, such as highly alkaline cleaners and domestic detergents, are aminopolyphosphonates, polycarboxylates or ethylenediaminetetraacetic acid (EDTA). The products undergo biodegradation only with difficulty, which is why there is a need for effective and, at the same time, low-cost substitutes which are readily biodegradable.

One alternative to the above substances is nitrilotriacetic acid (NTA) which is readily biodegradable but has distinct disadvantages in effect by comparison with EDTA and is often unwanted for toxicological reasons. Methylglycine-N,N-diacetic acid (α-alanine-N,N-diacetic acid, MGDA) is a nontoxic, readily biodegradable complexing agent with a higher stability constant than NTA. The use of MGDA and related glycine-N,N-diacetic acid derivatives for the detergents and cleaner sector and for numerous novel applications, and novel synthetic routes to such substances, are described in WO-A 94/29421 (1).

The synthesis of MGDA with the aid of chloroacetic acid has been known for a long time. This route is now no longer economic because of the unavoidable production of sodium chloride and the formation of organochlorine impurities, nor is it in accord with the times from the ecological standpoint. It is also necessary, in order to obtain high yields, to use excess chloroacetic acid, which is associated with the formation of glycolic acid, oxodiacetate and organochlorine compounds as byproducts. Other haloacetic acids result in a similar range of byproducts. The removal of the inorganic salts such as sodium chloride which are produced in stoichiometric amounts is elaborate and costly.

An economic and, at the same time, environmentally acceptable method for preparing aminopolycarboxylates is, in principle, the Strecker reaction of amino acids. The synthesis of MGDA by means of the Strecker reaction is described in (1).

DE-A 20 27 972 (2) describes the "acidic" variant of the Strecker reaction of unsubstituted glycine with formaldehyde and hydrocyanic acid. In this case, N,N-bis(cyanomethyl)glycine is formed from glycine and can be isolated in high purity, but the disadvantages of the described process are the need to use additional acid to reduce the pH and the use of costly pure glycine. The glycine-N,N-diacetonitrile formed in this case is described for use as crosslinker, but (2) does not relate to the possible hydrolysis to nitrilotriacetic acid. The conversion of alanine by the Strecker reaction to MGDA is described for the first time in (1), and in this case MGDA is obtained with high purity in high yields after hydrolysis, although once again only pure alanine is used. The high price for commercial pure amino acids such as alanine is a great economic hindrance to use in the synthesis of glycine-N,N-diacetic acids I.

The "alkaline" variant of the Strecker reaction is described in general form, for example, in U.S. Pat. No. 3,733,355 (3). However, the examples detailed therein show that a high proportion of byproducts, especially unwanted glycolic acid, always occurs; this can be concluded from the maximum conversions of only about 89%.

One advantage of the "acidic" over the "alkaline" variant of the Strecker reaction is the higher selectivity and the possibility of inserting an additional purification step, by isolating resulting nitrile compounds, and thus obtaining purer products.

U.S. Pat. No. 2,500,019 (4) mentions the reaction of α-amino acids with formaldehyde and sodium cyanide in general and, taking the example of unsubstituted protein hydrolysate, prepares nitrilotriacetic acid. However, the glycine which is the amino acid used in this process is particularly reactive because it is unsubstituted. In addition, the NTA which forms is, because of its high symmetry, thermodynamically preferred to nonsymmetrical compounds and is particularly easily formed.

The reaction of more sterically hindered amino acids such as alanine in high yields with minimal proportions of NTA is particularly difficult. Glycine sodium salt is prepared from protein hydrolysate in (4). A protein hydrolysate usually contains other amino acids in the mixture so that Strecker reaction does not given an NTA-pure product in this case.

The disadvantages of the method disclosed in (4) are the formation of byproducts, especially products of reactions of the ammonia which is produced, and the low stability of the starting materials at the high pH values which occur. The advantage of the one-stage procedure simultaneously results in the disadvantage of not being to isolate and purify intermediates.

It is an object of the present invention to provide a simple and economic synthetic route for glycine-N,N-diacetic acids such as MGDA starting from low-cost starting materials, where possible without interpolated purification steps, additionally aiming at a maximal overall yield with, at the same time, high product purities with low NTA contents, where possible below 2% by weight.

We have found that this object is achieved by a process for preparing glycine-N,N-diacetic acid derivatives of the general formula I

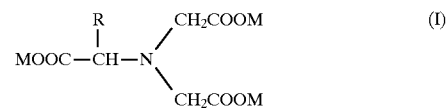 (I)

where

R is $C_1$–$C_{30}$-alkyl or $C_2$–$C_{30}$-alkenyl, each of which can additionally carry as substituents up to 5 hydroxyl groups, formyl groups, $C_1$–$C_4$-alkoxy groups, phenoxy groups or $C_1$–$C_4$-alkoxycarbonyl groups and can be interrupted by up to 5 nonadjacent oxygen atoms, or alkoxylate groups of the formula —$(CH_2)_k$—O—$(A^1O)_m$—$(A^2O)_n$—Y, where $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3 and m and n are each from 0 to 50, it being necessary for the total of m+n to be at least 4, phenylalkyl groups having 1 to 20 carbon atoms in the alkyl, phenyl, a five- or six-membered unsaturated or saturated heterocyclic ring which has up to three hetero atoms from the group consisting of nitrogen, oxygen and sulfur and which can additionally be benzo-fused, it also being possible for all the phenyl nuclei and heterocyclic rings mentioned in the meanings for R additionally to carry as substituents up to three $C_1$–$C_4$-alkyl groups, hydroxyl groups, carboxyl groups, sulfo groups or $C_1$–$C_4$-alkoxycarbonyl groups, or a radical of the formula

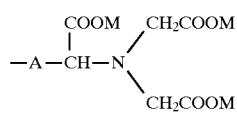

where A is a $C_1$–$C_{12}$-alkylene bridge or a chemical bond, and

M is hydrogen, alkali metal, alkaline earth metal, ammonium or substituted ammonium in the appropriate stoichiometric amounts, by reacting A) corresponding 2-substituted glycines or 2-substituted glycinonitriles or doubled glycines of the formula

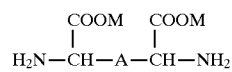

or doubled glycinonitriles of the formula

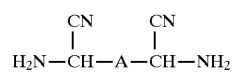

or precursors of the glycine derivatives named as starting material with formaldehyde and hydrogen cyanide in aqueous medium at a pH of from 0 to 11 or B) iminodiacetonitrile or iminodiacetic acid with appropriate monoaldehydes of the formula R—CHO or dialdehydes of the formula OHC—A—CHO and hydrogen cyanide in aqueous medium at a pH of from 0 to 11 and, where appropriate, subsequent hydrolysis of nitrile functionalities which are present, wherein the starting material used comprises raw material which has not been purified, ie. as a rule not isolated as solid or, for example, crystallized to remove additional constituents, and which derives from the industrial synthesis of glycine derivatives or their precursors or of iminodiacetonitrile or iminodiacetic acid, or mother liquors produced in such syntheses.

Precursors of glycine derivatives mean, for example in the case of alanine (R=$CH_3$), alanine amino nitrile or 5-methylhydantoin, the latter being produced, for example, by reaction of acetaldehyde, alkali metal cyanide and ammonium carbonate. The usual industrial synthesis of alanine is carried out by Strecker reaction of acetaldehyde, hydrocyanic acid and ammonia. Enzymatically prepared alanine can also be used without isolation of solid. Examples of noninterfering additional components which may be present in alanine mother liquors are lactic acid, alaninonitrile, 5-methylhydantoin, sodium sulfate, ammonium sulfate, sodium carbonate, phosphate buffer and other neutral buffers.

The reaction according to the invention of the glycine derivatives used or their precursors with formaldehyde and hydrogen cyanide in embodiment A is normally carried out at from 0° to 100° C., in partiuclar 10° to 80° C., especially 20° to 60° C. The pH of the aqueous reaction medium is from 0 to 11, preferably 1 to 8, ie. in the acidic or else in the weakly alkaline range.

It is expedient in embodiment A to use from 2.0 to 3.0, in particular 2.0 to 2.6, mol of formaldehyde, preferably in the form of its aqueous solution which is about 30% strength, and 2.0 to 3.0 mol, in particular 2.0 to 2.6 mol, of hydrogen cyanide per mole of glycine derivative, or its precursor, used as starting material. The starting material normally used comprises aqueous solutions of the appropriate glycine derivatives or precursors with a glycine derivative or precursor content of from 10 to 50% by weight, in particular 25 to 45% by weight.

The reaction in embodiment A is normally carried out by metering the formaldehyde and the hydrogen cyanide simultaneously over a period of from 0.1 to 12 hours, in particular 0.15 to 6 hours, especially 0.25 to 3 hours, into the glycine derivatives or their precursors at the stated reaction temperature and the stated pH. Reaction is then normally continued for from 1 to 20 hours, preferably 2 to 5 hours, under the reaction conditions.

The formaldehyde is normally used as aqueous solution. However, this component can also be added, for example, in solid form (eg. as paraformaldehyde). The reaction medium usually employed in embodiments A and B is water, which in most cases dissolves the final products and the reaction components used to a sufficient extent. However, it also possible to use mixtures of water and water-miscible organic solvents such as alcohols, eg. methanol, ethanol or isopropanol, when the intention is, for example, to prepare glycine-N,N-diacetic acids I with a more hydrophobic, ie. longer-chain or more voluminous, radical R.

The hydrolysis of nitrile functionalities which are present after the reaction to carboxylate groups is normally carried out with from 0.8 to 2.0, in particular 1.0 to 1.5, mole equivalents of aqueous sodium or potassium hydroxide solution per nitrile functionality under conventional conditions.

It is also possible and advantageous to use in embodiment B crude mixtures of iminodiacetonitrile and iminodiacetic acid or mother liquors which may be produced, for example, in the Strecker alanine synthesis. Noninterfering additional components in such mother liquors may be, for example, glycinonitrile, alaninonitrile, lactonitrile, glycolonitrile, methylenebisiminodiacetonitrile, ammonium sulfate, and nitrilotriacetonitrile in amounts <0.5% by weight.

The reaction according to the invention of iminodiacetonitrile or iminodiacetic acid with the appropriate aldehydes and hydrogen cyanide in embodiment B is carried out either by reacting crude iminodiacetonitrile or iminodiacetonitrile-containing mother liquors with aldehyde and HCN to give the corresponding glycinonitrile-N,N-diacetonitrile and subsequent alkaline hydrolysis to the compounds I (route a) or by alkaline hydrolysis of iminodiacetonitrile to iminodiacetic acid and subsequent reaction with the aldehyde and HCN to give compounds I (route b).

Iminodiacetonitrile itself can easily be obtained, for example, by known processes from aqueous Urotropin by reaction with hydrogen cyanide (6 to 8 mole equivalents) in a mineral acid medium (pH 3 to 8) at 20° to 100° C. However, iminodiacetonitrile can also advantageously be produced directly from the appropriate amounts of formaldehyde, ammonia and HCN in, for example, aqueous sulfuric acid.

In route (a), as a rule, the iminodiacetonitrile, preferably as 5 to 30% by weight mother liquor, is reacted with from 0.8 to 3.0 mol, in particular 1.0 to 1.5 mol, of hydrogen cyanide and, at the same or a different time, with from 0.8 to 3.0 mol, in particular 1.0 to 1.5 mol, of the aldehyde in aqueous medium with a pH of, preferably, :0 to 5, which is normally adjusted by adding mineral acids, at from 0° to 100° C., in particular 20° to 60° C., over the course of from 0.5 to 12 hours, in particular 1 to 5 hours, and reaction is then allowed to continue for, normally, from 0.5 to 20 hours, in particular 2 to 6 hours, under the reaction conditions. Subsequently, where appropriate after isolation of the intermediate by filtration or decantation, hydrolysis is normally carried out with from 2 to 5 mole equivalents, in particular 3 to 4 mole equivalents, of aqueous sodium or potassium hydroxide solution, based on iminodiacetonitrile used, under conventional conditions.

In route (b), the resulting iminodiacetonitrile is, where appropriate after removal by filtration or decantation, normally hydrolyzed with from 1.8 to 3.0 mole equivalents, in particular 2.0 to 2.5 mole equivalents, of aqueous sodium or potassium hydroxide solution under conventional conditions, followed by acidification with mineral acids expediently to pH 1–8. Thereafter the resulting iminodiacetic acid is reacted as a rule with from 0.8 to 2.0 mol, in particular 1.0 to 1.5 mol, of hydrogen cyanide and, at the same or a different time, with from 0.8 to 2.0 mol, in particular 1.0 to 1.5 mol, of the aldehyde, in each case based on iminodiacetonitrile used, at from 0° to 100° C., in particular 20° to 60° C., over the course of from 1 to 20 hours, in particular 2 to 6 hours, and reaction is then allowed to continue for, normally, from 1 to 20 hours, in particular 2 to 10 hours, under the reaction conditions. Finally, hydrolysis is carried out, normally with from 0.8 to 2.0 mole equivalents, in particular 1.0 to 1.5 mole equivalents, of aqueous sodium or potassium hydroxide solution, based on iminodiacetonitrile used, under conventional conditions to give the compounds I.

It has proven expedient in the hydrolysis steps in the process according to the invention in embodiment A or B to reduce the pressure, before and/or during the reaction, to from 100 to 1000 mbar, preferably 300 to 900 mbar, in particular 500 to 800 mbar, in the reaction apparatus. It is furthermore possible, in addition to this or else as separate measure before and/or during a hydrolysis step, to pass an inert gas such as air, nitrogen or argon through the reaction mixture or the mixed reactants (inert gas stripping). The reduction in pressure and the passing through of inert gas serve, in particular, to improve removal from the reaction system of the ammonia still present in the precursors or formed during the hydrolysis.

The process according to the invention can be used with particularly good results for preparing glycine-N,N-diacetic acid derivatives I where R is $C_1$–$C_{20}$-alkyl, $C_2$–$C_{20}$-alkenyl or a radical of the formula

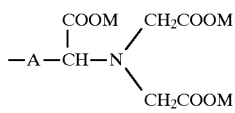

The process according to the invention is very particularly suitable for preparing α-alanine-N,N-diacetic acid (R=CH$_3$) and its alkali metal, ammonium and substituted ammonium salts.

Particularly suitable salts of this type are the sodium, potassium and ammonium salts, especially the trisodium, tripotassium and triammonium salt, and organic triamine salts with a tertiary nitrogen atom.

Particularly suitable bases on which the organic amine salts are based are tertiary amines such as trialkylamines with from 1 to 4 carbon atoms in the alkyl, eg. trimethylamine and triethylamine, and trialkanolamines with 2 or 3 carbon atoms in the alkanol residue, preferably triethanolamine, tri-n-propanolamine or triisopropanolamine.

Calcium and magnesium salts are used in particular as alkaline earth metal salts.

Besides methyl, suitable straight-chain or branched alk(en)yl radicals for R are, in particular, $C_2$–$C_{17}$-alkyl and -alkenyl, of these in particular straight-chain radicals derived from saturated or unsaturated fatty acids. Examples of individual R radicals are: ethyl, n-propyl, isopropyl, n-butyl, isobutyl, sec-butyl, tert-butyl, n-pentyl, isopentyl, sec-pentyl, tert-pentyl, neopentyl, n-hexyl, n-heptyl, 3-heptyl (derived from 2-ethylhexanoic acid), n-octyl, isooctyl (derived from isononanoic acid), n-nonyl, n-decyl, n-undecyl, n-dodecyl, isododecyl (derived from isotridecanoic acid), n-tridecyl, n-tetradecyl, n-pentadecyl, n-hexadecyl, n-heptadecyl, n-octadecyl, n-nonadecyl, n-eicosyl and n-heptadecenyl (derived from oleic acid). Mixtures may also occur for R, especially those derived from naturally occurring fatty acids and from synthetic industrial acids, for example from the oxo synthesis.

Examples of the $C_1$–$C_4$-, $C_1$–$C_{12}$- and $C_1$–$C_{20}$-alkyl groups which are also mentioned are also to be regarded as the corresponding radicals detailed above for R.

Used as $C_1$–$C_{12}$-alkylene bridges A are, in particular, polymethylene groups of the formula —(CH$_2$)$_k$— where k is from 2 to 12, in particular from 2 to 8, ie. 1,2-ethylene, 1,3-propylene, 1,4-butylene, pentamethylene, hexamethylene, heptamethylene, octamethylene, nonamethylene, decamethylene, undecamethylene and dodecamethylene. Hexamethylene, octamethylene, 1,2-ethylene and 1,4-butylene are particularly preferred. However, branched $C_1$–$C_{12}$-alkylene groups may also occur, eg. —CH$_2$CH(CH$_3$)CH$_2$—, —CH$_2$C(CH$_3$)$_2$CH$_2$—, —CH$_2$CH(C$_2$H$_5$)— or —CH$_2$CH(CH$_3$)—.

The $C_1$–$C_{30}$-alkyl and $C_2$–$C_{30}$-alkenyl groups may carry up to 5, in particular up to 3, additional substituents of the said type and be interrupted by up to 5, in particular up to 3, nonadjacent oxygen atoms. Examples of such substituted alk(en)yl groups are —CH$_2$OH, —CH$_2$CH$_2$OH, —CH$_2$CH$_2$—O—CH$_3$, —CH$_2$—CH$_2$—O—CH$_2$CH$_2$—O—CH$_3$, —CH$_2$—O—CH$_2$CH$_3$, —CH$_2$—O—CH$_2$CH$_2$—OH, —CH$_2$—CHO, —CH$_2$—OPh, —CH$_2$—COOCH$_3$ or CH$_2$CH$_2$—COOCH$_3$.

Particularly suitable alkoxylate groups are those where m and n are each from 0 to 30, in particular from 0 to 15. $A^1$ and $A^2$ are groups derived from butylene oxide and, in particular, from propylene oxide and from ethylene oxide. Pure ethoxylates and pure propoxylates are of particular interest, but ethylene oxide/propylene oxide block structures may also occur.

Suitable five- or six-membered unsaturated or saturated heterocyclic rings which have up to three hetero atoms from the group consisting of nitrogen, oxygen and sulfur and which can additionally be benzo-fused and substituted by the identified radicals are:

tetrahydrofuran, furan, tetrahydrothiophene, thiophene, 2,5-dimethylthiophene, pyrrolidine, pyrroline, pyrrole, isoxazole, oxazole, thiazole, pyrazole, imidazoline, imidazole, 1,2,3-triazolidine, 1,2,3- and 1,2,4-triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazane, pyridine, α-, β- and γ-picoline, α- and γ-piperidone, pyrimidine, pyridazine, pyrazine, 1,2,5-oxathiazine, 1,3,5-, 1,2,3- and 1,2,4-triazine, benzofuran, thionaphthene, indoline, isoindoline, benzoxazole, indazole, benzimidazole, chroman, isochroman, 2H- and 4H-chromene, quinoline, isoquinoline, 1,2,3,4-tetrahydroisoquinoline, cinnoline, quinazoline, quinoxaline, phthalazine and benzo-1,2,3-triazine.

N-H groups in said heterocyclic rings ought where possible to be present in derivatized form, for example as N-alkyl groups.

Substituted phenyl nuclei or heterocyclic rings preferably have two (identical or different) or, in particular, a single substituent.

Examples of unsubstituted or substituted phenylalkyl groups and alkyl groups carrying heterocyclic rings for R are benzyl, 2-phenylethyl, 3-phenylpropyl, 4-phenylbutyl, o-, m- or p-hydroxylbenzyl, o-, m- or p-carboxylbenzyl, o-, m- or p-sulfobenzyl, o-, m- or p-methoxy- or -ethoxycarbonylbenzyl, 2-furylmethyl, N-methyl-4-piperidinylmethyl or 2-, 3- or 4-pyridinylmethyl.

Preferred substituents on phenyl nuclei and on heterocyclic rings are groups which confer solubility in water, such as hydroxyl groups, carboxyl groups or sulfo groups.

The compounds I prepared by the process according to the invention may be in the form of racemates or of enantiomerically pure compounds in respect of the α-carbon atom, depending on whether D,L-glycine derivatives or the corresponding D or L forms are used as starting material in embodiment A. Embodiment B usually results in the racemates of I.

The free acids of compounds I can, if the compounds I result in the form of salts, be obtained by acidification by conventional methods.

The specific way of carrying out the reaction in the process according to the invention very substantially suppresses the formation of unwanted NTA in the product, and the amounts of NTA are distinctly less than 2% by weight, usually 0.1–0.3% by weight. In a similar way, the formation of nitrilotriacetonitrile is suppressed in embodiment B.

It is precisely because mother liquors are used in the process according to the invention that it is possible to avoid the workup loss in the isolation of the glycine derivatives or their precursors or in the isolation of iminodiacetonitrile. It is likewise possible to avoid the hydrolysis of a nitrile intermediate which is otherwise required as separate intermediate step. This makes the process according to the invention considerably more economic. The efficiency of the conversion of the starting compounds in mother liquors is surprisingly not impaired by comparison with conversion of the pure starting compounds so that the increase in the overall yield is usually from 5 to 15%. The central aspect of the process according to the invention is the possibility of using in place of pure glycine derivatives or pure iminodiacetonitrile or pure iminodiacetic acid also crude mixtures resulting from the Strecker amino acid synthesis, for example of alanine, or else enzymatically, but also corresponding precursors such as hydantoins. This procedure is particualrly economic because the costly product removal at the isoelectric point which is normally necessary following the amino acid preparation is unnecessary in this case. It is thus possible to save on reagents for adjusting the pH and to avoid separation losses because the amino acid normally remaining in the mother liquor of the amino acid synthesis is also used. It is possible and beneficial for the alkali metal salt from the amino acid synthesis to be reacted directly, without further addition of alkali, and without loss of yield and selectivity. Hydantoins can just like nitriles be hydrolyzed in a mixture by adding the appropriate amount of alkali and be directly reacted in one step with formaldehyde and hydrogen cyanide in the manner according to the invention, and this method overall provides a higher total yield with, at the same time, a simpler process compared with reaction of amino acid isolated by precipitation.

The particular procedure for the process according to the invention also permits the synthesis to be carried out not only batchwise but also continuously, starting from basic chemicals which are available at low cost, such as formaldehyde, acetaldehyde, hydrocyanic acid, ammonia and sodium hydroxide solution, in a sequence of consecutive reaction stages, with no impairment of yield and purity in, at the same time, a particularly economic manner. In particular, the conversion of iminodiacetonitrile into glycinonitrile-N, N-diacetonitrile (route a) and subsequent hydrolysis to I are suitable for a continuous process of this type. The continuous procedure surprisingly reduces even further, especially in the hydrolysis, the NTA content in the final product.

EXAMPLES

Example 1

Preparation of MGDA trisodium salt from crude alanine mixture 28.5 g of hydrocyanic acid (99.3% by weight) and 105 g of formaldehyde (30% by weight, aqueous) were simultaneously added dropwise to a suspension of 44 g of D,L-alanine prepared by reacting 27.5 g of acetaldehyde with 17 g of hydrocyanic acid (99.3% by weight) in 128 g of 25% by weight aqueous ammonia at 20° C. for 2 h and subsequent hydrolysis with 50 g of 50% by weight aqueous sodium hydroxide solution at 20° C. for 20 h, with nitrogen stripping at 95° C. for 3 h and subsequent neutralization to pH 6 with 44 g of 50% by weight aqueous sulfuric acid, and the mixture was then stirred at 30° C. for 3 h. The decrease in hydrocyanic acid corresponded to 98% of theory based on alanine.

This solution was then added dropwise to 103 g of 50% by weight aqueous sodium hydroxide solution at 30° C., and the mixture was stirred at 30° C. for 4 h and at 95° C. while stripping with nitrogen for a further 6 h. The result was 389 g of an aqueous solution of MGDA trisodium salt, which was 33.4% by weight according to the iron-binding capacity, corresponding to a yield of 95% based on alanine. The overall yield was thus 77%, compared with 69% with previous isolation of alanine. The NTA content in the solution was 0.1% by weight.

Example 2

Preparation of MGDA trisodium salt from crude alaninonitrile mixture 27.2 g of hydrocyanic acid (99.3% by weight) were added dropwise to 204 g of 25% by weight aqueous ammonia at 0° C. Then, over the course of 20 min, 44 g of acetaldehyde were added dropwise to the resulting solution at 0° to 10° C. and, after a further 2 h at 20° C., the HCN conversion was 98%, after which the solution was stripped with nitrogen under 200 mbar for 1 h. The pH was then adjusted to 2 with 69 g of 98% by weight sulfuric acid and, over the course of 30 min, 55 g of hydrocyanic acid (99.3% by weight) and 200 g of formaldehyde (30% by weight, aqueous) were simultaneously added dropwise, after which the mixture was stirred at 50° C. for 8 h. After cooling, a total of 115 g, corresponding to 78% of theory, of methylglycinonitrile-N, N-diacetonitrile precipitated as a colorless solid. Introduction of this precipitate into 471 g of 20% by weight aqueous sodium hydroxide solution at 40° C. and then stirring at this temperature for 3 hours and at 95° C. (with simultaneous stripping with nitrogen) for a further 5 h resulted in 553 g of an aqueous solution of MGDA trisodium salt, which was 35% by weight according to the iron-binding capacity, corresponding to an overall yield of 72% of theory. The NTA content of the solution was 0.07% by weight.

Example 3

Preparation of MGDA trisodium salt from crude iminodiacetonitrile mixture (route a)

284 g of 25% by weight aqueous ammonia were added to 600 g of 30% by weight aqueous formaldehyde, and subsequently the pH was adjusted to 6 with sulfuric acid and then, at 50° C., 170 g of hydrocyanic acid (99.1% by weight) and further sulfuric acid to maintain the above pH were added. After a total of 4 h, the pH was adjusted to 1.5 by adding sulfuric acid and, at the same time, 82 g of hydrocyanic acid (99.1% strength) and 132 g of acetaldehyde were added. After 4 h, 408 g of methylglycinonitrile-N,N-diacetonitrile were obtained as crystals, corresponding to 92% of theory.

Introduction of this precipitate into 1670 g of 20% by weight aqueous sodium hydroxide solution at 40° C., followed by stirring at this temperature for 3 hours and at 95° C. (with simultaneous stripping with nitrogen) for a further 5 h resulted in 1960 g of an aqueous solution of MGDA trisodium salt, which was 35% by weight according to the iron-binding capacity, corresponding to an overall yield of 85% of theory. The NTA content of the solution was 0.08% by weight. By comparison, an overall yield of only 70% was obtained with intermediate isolation of iminodiacetonitrile.

Example 4

Preparation of MGDA trisodium salt from crude iminodiacetic acid mixture (route b)

95 g of iminodiacetonitrile were introduced into 420 g of 50% by weight aqueous sodium hydroxide solution at 40° C. and, after 2 h, the mixture was heated at 95° C. for 5 h. The resulting disodium iminodiacetate solution was then adjusted to pH 6 with 49 g of sulfuric acid (98% by weight) and subsequently, at 30° C., 28.5 g of hydrocyanic acid (99.3% by weight) and 46 g of acetaldehyde were simultaneously added dropwise, after which the mixture was stirred at 60° C. for 8 h. The decrease in hydrocyanic acid corresponded to 95% of theory.

This solution was then added dropwise to 84 g of 50% by weight aqueous sodium hydroxide solution at 30° C., and the mixture was stirred at 30° C. for 4 h and at 95° C. while stripping with nitrogen for a further 6 h. The result was 661 g of an aqueous solution of MGDA trisodium salt, which was 36.5% by weight according to the iron-binding capacity, corresponding to an overall yield of 89%, compared with 84% with previous isolation of iminodiacetic acid. The NTA content in the solution was 0.32% by weight.

We claim:

1. A process for preparing a glycine-N,N-diacetic acid derivative of the formula I

where

R is $C_1$–$C_{30}$-alkyl or $C_2$–$C_{30}$-alkenyl, each of which can additionally carry as substituents up to 5 hydroxyl groups, formyl groups, $C_1$–$C_4$-alkoxy groups, phenoxy groups or $C_1$–$C_4$-alkoxycarbonyl groups and can be interrupted by up to 5 nonadjacent oxygen atoms, or alkoxylate groups of the formula —$(CH_2)_k$—O—$(A^1O)_m$—$(A^2O)_n$—Y, where $A^1$ and $A^2$ are, independently of one another, 1,2-alkylene groups having 2 to 4 carbon atoms, Y is hydrogen, $C_1$–$C_{12}$-alkyl, phenyl or $C_1$–$C_4$-alkoxycarbonyl, and k is 1, 2 or 3 and m and n are each from 0 to 50, it being necessary for the total of m+n to be at least 4, phenylalkyl groups having 1 to 20 carbon atoms in the alkyl, phenyl, a five- or six-membered unsaturated or saturated heterocyclic ring which has up to three hetero atoms from the group consisting of nitrogen, oxygen and sulfur and which can additionally be benzo-fused, or a radical of the formula

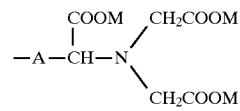

where A is a $C_1$–$C_{12}$-alkylene bridge or a chemical bond, and

M is hydrogen, alkali metal, alkaline earth metal, ammonium or substituted ammonium in the appropriate stoichiometric amounts, comprising reacting an unpurified raw material of:

a) i) a corresponding 2-substituted glycine;
ii) a corresponding 2-substituted glycinonitrile;
iii) the formula

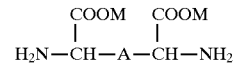

or iv) the formula

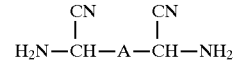

wherein A is defined as above, with formaldehyde and hydrogen cyanide in aqueous medium at a pH of from 0 to 11 and hydrolysis of nitrile functionalities when present; or b) of iminodiacetonitrile or iminodiacetic acid with a monoaldehyde of the formula R—CHO or a dialdehyde of the formula OHC—A—CHO wherein R and A are as defined above and hydrogen cyanide in aqueous medium at a pH of from 0 to 11 and hydrolysis of nitrile functionalities when present.

2. A process for preparing glycine-N,N-diacetic acid derivatives I as claimed in claim 1, where R is $C_1$–$C_{20}$-alkyl, $C_2$–$C_{20}$-alkenyl or a radical of the formula

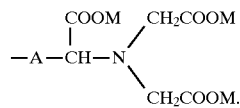

3. The process of claim 1, wherein said unpurified raw material is obtained by the Strecker synthesis.

4. The process of claim 1, wherein said unpurified raw material is obtained enzymatically.

5. The process of claim 1, wherein R is $CH_3$.

* * * * *